United States Patent [19]
Imaino et al.

[11] Patent Number: 5,898,492
[45] Date of Patent: Apr. 27, 1999

[54] SURFACE INSPECTION TOOL USING REFLECTED AND SCATTERED LIGHT

[75] Inventors: Wayne Isami Imaino; Milton Russell Latta, both of San Jose, Calif.

[73] Assignee: International Business Machines Corporation, Armonk, N.Y.

[21] Appl. No.: 08/937,886

[22] Filed: Sep. 25, 1997

[51] Int. Cl.$^6$ .................................................. G01N 21/88
[52] U.S. Cl. ................................... 356/237.1; 356/237.5; 356/237.2
[58] Field of Search ................... 356/237, 239, 356/394, 431–432, 430

[56] References Cited

U.S. PATENT DOCUMENTS

| | | | |
|---|---|---|---|
| 2,806,401 | 9/1957 | Demuth et al. | 356/237 |
| 3,790,287 | 2/1974 | Cuthbert et al. | 356/120 |
| 4,358,202 | 11/1982 | Puffer et al. | 356/430 |
| 4,441,124 | 4/1984 | Heebner et al. | 356/237 |
| 4,464,050 | 8/1984 | Kato et al. | 356/237 |
| 4,610,541 | 9/1986 | Tanimoto et al. | 356/237 |
| 4,720,191 | 1/1988 | Siegel et al. | 356/237 |
| 4,794,265 | 12/1988 | Quackenbos et al. | 250/572 |
| 4,861,164 | 8/1989 | West | 356/445 |
| 4,954,723 | 9/1990 | Takahashi et al. | 250/572 |
| 5,076,692 | 12/1991 | Neukermans et al. | 356/538 |
| 5,125,741 | 6/1992 | Okada et al. | 356/237 |
| 5,200,799 | 4/1993 | Maruyama et al. | 356/394 |
| 5,220,617 | 6/1993 | Bird et al. | 382/8 |
| 5,381,225 | 1/1995 | Kohno | 356/431 |
| 5,448,364 | 9/1995 | Moran | 356/430 |
| 5,523,846 | 6/1996 | Haga | 356/445 |
| 5,528,360 | 6/1996 | Kohno | 356/237 |
| 5,581,353 | 12/1996 | Taylor | 356/381 |

FOREIGN PATENT DOCUMENTS

| | | | |
|---|---|---|---|
| 59-073710 | 4/1984 | Japan | G01B 11/30 |
| 2-132311 | 11/1988 | Japan | G01B 11/24 |
| 1-257250 | 10/1989 | Japan | G01N 21/88 |
| 7-198622 | 8/1995 | Japan | G01N 21/88 |

OTHER PUBLICATIONS

C. J. Kircher et al., "Surface Optical Relectance Process Monitor", IBM Technical Disclosure Bulletin, vol. 19, No. 12, May 1977, pp. 4806–4810.

D. C. Forslund et al., "Dual Laser Reflective Scanner", IBM Technical Disclosure Bulletin, vol. 30, No. 7, Dec. 1987, pp. 6–7.

C. A. Gaston et al., "Visually Aligned Monochromatic Lamina Detector", IBM Technical Disclosure Bulletin, vol. 20, No. 3, Aug. 1977, pp. 1022–1023.

IEEE/SEMI 1995 Advanced Semiconductor Manufacturing Conference and Workshop, ASMC 95 Proceedings, "Theme—Semiconductor Manufacturing: Economic Solutions for the 21st Century", Nov. 13–15, 1995, Cambridge, Massachusetts.

*Primary Examiner*—Hoa Q. Pham
*Attorney, Agent, or Firm*—G. Marlin Knight

[57] ABSTRACT

A laser based inspection tool is described which is particularly useful for inspecting one or both planar surfaces of disks for use in disk drives. The tool uses low angle reflected light and large angle scattered (LAS) light from the surface which are separately detected and pixelated to create a reflected light image and a scattered light image. The tool uses a mechanical lifter which moves the disk through the laser scan lines to allow the surface on one or both sides of the disk to be scanned. The line scanning is performed using a rotating polygon mirror (scanner) which also captures the beam reflected from the disk surface. A telecentric lens assembly (TLA) acts to ensure that the laser beam is incident at a substantially constant, nearly perpendicular angle as the beam scans across the disk and to direct the reflected and scattered light back onto the scanner. The LAS light is captured by a pair of plano mirrors disposed above and below the scan line. The two cones of LAS light from the plano mirrors are directed back through the TLA along with the reflected light onto the polygon. The LAS light is then separated from the reflected light by a beam splitter and the intensities of the two separated beams are converted into sampled digital values which are processed to form two images of the surface. These two images are used in combination to detect defects in the disk surface and to avoid false rejections. The LAS image is useful in determining that deviations in the reflected light are likely to be a particle adhering to the surface and not a true defect. The LAS image and the reflected light image are available for various types of analysis and comparison making the tool adaptable for a wide variety of surface inspection techniques.

16 Claims, 9 Drawing Sheets

SURFACE INSPECTION TOOL USING REFLECTED AND SCATTERED LIGHT

RELATED APPLICATIONS

A set of related, commonly assigned applications which describe a surface inspection tool having some common features with the apparatus described in this application are assigned Ser. Nos. 08/840,351; 08/841,214; 08/840,354; 08/840,358; 081841,037; 08/840,352; 08/840,355 and 08/840,339.

FIELD OF THE INVENTION

The invention relates to the field of precision surface analysis for defects. More particularly the invention relates to laser based tools for obtaining data on surface features by optical means.

BACKGROUND

Magnetic and optical disks require precision surfaces with extremely low defect rates to function properly. A typical magnetic disk comprises a substrate on which multiple layers of various materials are deposited. For example, an aluminum substrate might be coated electrolessly with NiP then sputtered with thin films of Cr as an undercoat, a cobalt alloy magnetic layer and a hydrogenated carbon overcoat. Depending on the stage of the process these surfaces are not necessarily uniform. For example, after the NiP has been applied a small circular band on the surface of the disk may be textured using a laser to form microscopic bumps. This textured region is intended to provide a low stiction area for the sliders to rest during nonoperating periods. In addition to intentional variations there may be various types of defects. As the disks progress through the manufacturing process various tests and inspections are used to detect defective disks so that they may either be reworked or discarded. In addition to visual inspections, a disk may be subjected to glide tests which are sensitive to the flatness of the planar surfaces, as well as magnetic read/write tests. Due to high capacities of magnetic disks it is typically not practical to magnetically test each bit which can be stored on the disk.

Laser surface inspection of the disks if sufficiently precise may actually be superior to current magnetic tests in detecting defects. Magnetic defects are usually associated with visible defects, but the visible defects can be detected more efficiently through laser inspection even though the laser spot size is considerably larger than the area in which a bit can be recorded. Thus, laser inspection allows greater test coverage of the disk in a cost effective manner.

Various laser inspection devices are known in the art. Commonly assigned U.S. Pat. No. 5,220,617 by Bird, et al. describes a laser scanner for green sheets to detect via errors. The sheets are moved on an air track to a transport table which translates them as the scan occurs. Only one side is scanned. The system uses a rotating polygon mirror to scan and to capture the reflected light. The bright field reflected light is captured at the hole-in-plate splitter and directed to a single fibre. This channel detects contrast between the conductive paste and the green sheet. The dark field reflected light is captured by fibers located near the surface of the object. The incident light is perpendicular, but there is a suggestion that other angles are possible. There is a start of scan mirror adjacent to the object, but its function is said to be to provide an initialization or start/stop point. The reference signal is obtained from the initial part of the green sheet. The lens assembly is a flat field telecentric anamorphic f-theta lens system. The f-theta condition corrects for the pincushion distortion. A focusing telescope converges the image down to a slit. The shaping lens system results in a collimated bundle 10.8 mm by 130 microns on the polygon. This shape is said to be selected for pickup by the fiber bundles.

SUMMARY OF THE INVENTION

The invention will be described as embodied in a laser based inspection tool (LIT) for inspecting one or both planar surfaces of disks for use in disk drives, but the invention may be employed in any system for inspecting a planar surface. The LIT uses low angle specularly reflected light and large angle scattered light (LAS) from the surface which are separately detected and pixelated to create a reflected light image, as well as, a scattered light image.

The LIT uses a mechanical lifter which moves the disk through the laser scan lines to allow the surface on one or both sides of the disk to be scanned. The line scanning is performed using a rotating polygon mirror (also called a scanner) which also captures the beam reflected from the disk surface. A telecentric lens assembly (TLA) acts to ensure that the laser beam is incident at a substantially constant, nearly perpendicular angle as the beam scans across the disk and to direct the reflected and scattered light back onto the scanner. The LAS light is captured by at least one and preferably a pair of plano mirrors disposed above and below the scan line. The two cones of LAS light from the plano mirrors are directed back through the TLA along with the reflected light onto the scanner. The LAS light is then separated from the specularly reflected light by a beam splitter and the intensity of the two separated beams is converted into sampled digital values which are processed to form two images of the surface. These two images are used in combination to detect defects in the disk surface and to avoid false rejections. The LAS image is useful in determining that deviations in the reflected light are likely to be a particle adhering to the surface and not a true defect in the surface. The LAS image and the specularly reflected light image are available for various types of analysis and comparison making the tool easily adaptable for a wide variety of surface inspection applications.

DETAILED DESCRIPTION OF THE PREFERRED EMBODIMENTS

The preferred embodiments of the invention will be described in relation to a laser based inspection tool for inspecting the planar surfaces of disks for use in disk drives, but the invention may be employed in any system for inspecting a planar surface. The inspection is preferably performed on both surfaces of the disk simultaneously for efficiency. The Laser Inspection Tool (LIT) is general in that it can be used to inspect any sufficiently smooth flat surface at any stage of the process; therefore, it could be used to inspect raw or initial substrates, substrates after nickel-phosphorous plating or finished disks. The LIT uses low angle reflected light in addition to large angle scattered light (LAS) from the surface to allow absolute reflectivity measurements if desired and to aid in the detection of certain types of disk defects such as stains which do not effect the scattering of the light and to descriminate between nonattached (loose) particles on the surface and actual defects in the surface. Stain detection is accomplished through the use of derivative analysis of the reflected light to detect the change in the reflectivity of the surface associated with a disk stain. The system is designed to preserve both the polarization and the wave vector of the reflected light which allows it to be used with minor modifications in a broad range of applications. Using a stable laser, low noise detectors and sufficiently high resolution A/D converters, it is possible to detect a change in reflectivity of approximately 0.1% in a 1 MHz bandwidth using the LIT. A mechanical lifter holds the disk so that the two planar surfaces are perpendicular to the beam and moves the disk through the laser scan lines to allow substantially all of the planar surface on each side of the disk to be scanned. The line scanning uses a rotating mirror (scanner) which is also used to direct the beam reflected from the disk surface, as well as, the LAS light from the two plano mirrors. The two plano mirrors (LAS mirrors) arranged above and below the scan line provide a constant collection aperture along the entire scan line for all angular positions of the polygon scanner. The LAS mirrors should be wide enough to collect a significant angular cone of the LAS light and oriented to direct the cones of LAS light back onto the polygon facet.

As the disk is lifted into the scanning area it can optionally be passed through a pair of air knives which attempt to blow loose particles from both surfaces, but there may be particles which are attached to the surface electrostically or otherwise in such a way that they cannot be blown off or which re-attach themselves after temporarily being blown off. The use of the LAS light is especially helpful in distinguishing these surface particles from true surface defects.

Figure 1:
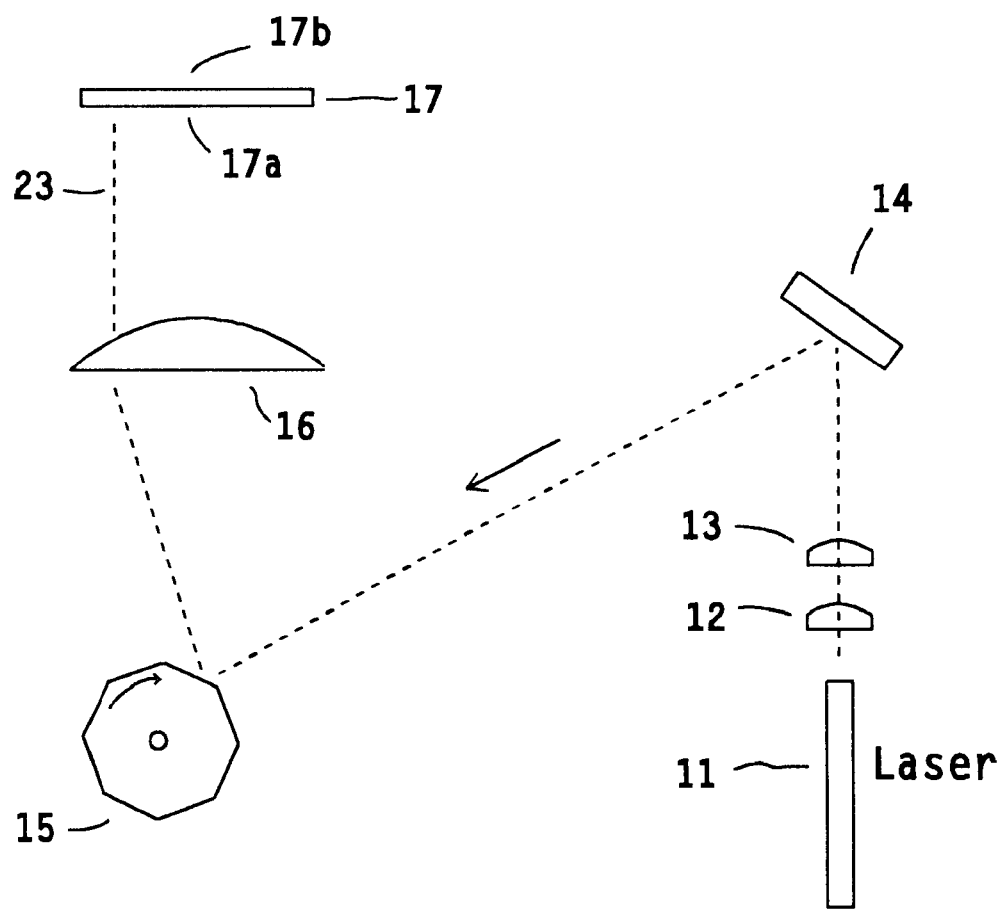
FIG. 1 shows the optical elements in the beam path from the laser source to the surface to be inspected.

FIG. 1 shows the optical path elements for a preferred embodiment of the optical system of one channel (the A-channel) of the LIT from the laser source 11 to the disk 17 and the disk surface 17a. The elements in the second channel (the B-channel) for inspecting the other surface 17b are identical, but are preferably arranged in a mirror image of the A-channel elements and in the same plane. The A and B-channels can be assembled on a single baseplate. The choice of low power laser is not critical, e.g. GaAs, HeNe, etc. are acceptable, but it is preferable that the wavelength be in the visible spectrum for aiding alignment. The use of an unpolarized laser is preferable, since it reduces sensitivity to the orientation of defects such as scratches. A few milliwatts of power is sufficient. Since high sensitivity to absolute amount of reflected light is a goal in the design of the LIT, it is important to select a laser, e.g. HeNe, to minimize noise which might be injected into the system through laser instability. In the preferred embodiment separate lasers are used for each channel, but it is also possible to use a single laser source with a beam splitter. Lenses 12 and 13 form a telescope (beam expander) which is used to expand the beam 23 (the incident beam). The term incident beam (or A-beam to specify the A-channel) will be used to refer to all segments of the laser beam from generation at the laser 11 along the path to the surface of the disk being inspected (or as will be noted later an optional calibration mirror). Steering mirror 14 reflects the beam onto the rotating polygon scanner 15 which reflects into the telecentric lens assembly (TLA) 16. As will be seen there is a beam splitter in the path between mirror 14 and the scanner, but it is not shown in this figure since it does not affect the incident beam. The TLA acts to keep the laser beam incident at a constant nearly perpendicular angle as the beam scans across the disk. The TLA is designed to have a very flat field curvature through the scanning line to keep the spot size sufficiently constant for accurate detection. The figure shows the polygon scanner 15 rotating in a clockwise direction which will cause the incident beam to sweep from left to right across the TLA and in turn to scan a line across the planar surface of the disk. Each mirrored facet of the polygon corresponds to one scan line across the disk. The choice of a polygon scanner is preferred, but other scanning means such as a galvonometer mirror could be used. The view of FIG. 1 can be considered to be a top view which shows only the top edge of the disk or other item having the planar surface to be inspected. The system could be mounted either vertically or horizontally, so "top view" is used as a relative term. The TLA should have a usable optical scan line which is at least equal to and preferably slightly longer than the desired scan length. A laser spot size on the disk of approximately 50 microns in diameter provides sufficient resolution for detecting defects in current disks. Smaller spot size can be used to increase the maximum resolution of the system if desired by altering the focal lengths of the telescope lenses.

Figure 2:
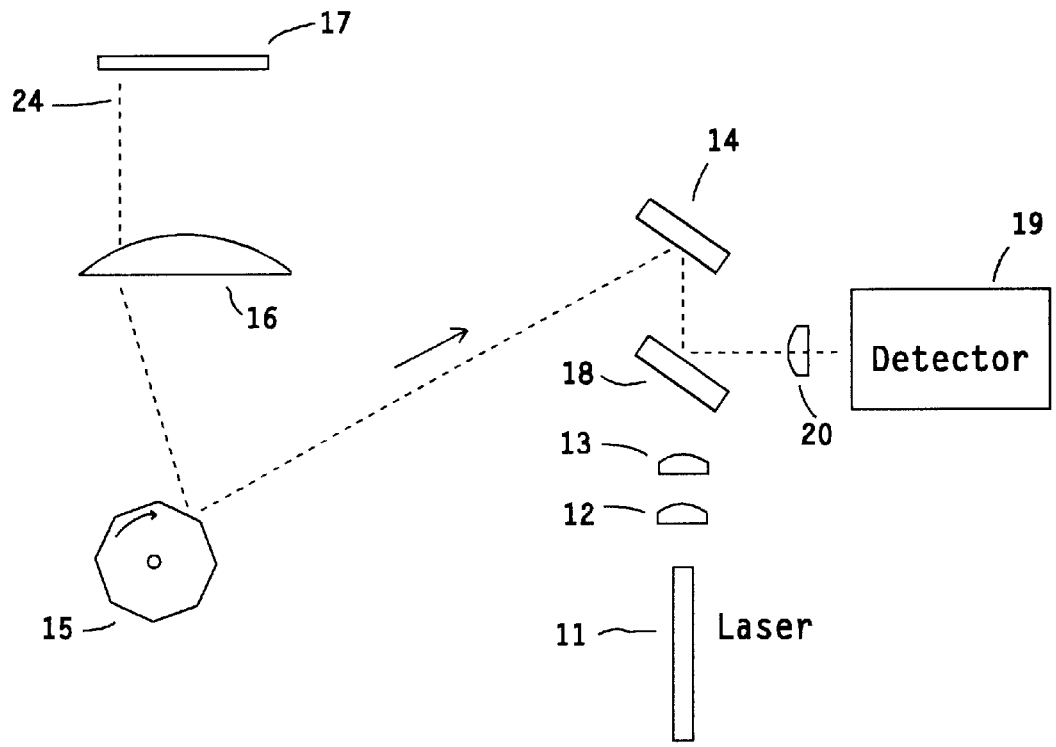
FIG. 2 shows the optical elements in the path for the reflected beam from the surface being inspected.

FIG. 2 shows the optical elements in the path for the reflected beam 24 from the surface being inspected. The term reflected beam (or A/R-beam) will be used to refer to all segments of the beam which are reflected from the object's surface as it follows the path to the detector. The surface of the object 17 reflects a portion of the incident beam to form a reflected beam 24 which follows a path back through the LIT which is slightly offset from the path of the incident beam. (Note: The described embodiment inspects the planar surfaces of disks, but nonplanar surfaces could be inspected using the system if the nonplanarity is no more than a few degrees.) The reflected beam passes through the TLA 16 and is reflected by the scanner 15 back to mirror 14. As noted for the incident beam the reflected beam passes through a beam splitter in the path between the scanner and mirror 14, but it is not shown in figure since it does not affect the reflected beam. Because the path of the reflected beam is offset from the incident beam the reflected beam strikes capture mirror 18 which diverts the reflected beam through lens 20 which reduces the spot size of the beam striking detector 19. The detector is preferably a silicon detector which produces an analog signal which is a function of the amplitude or intensity of the reflected beam. The detector should have very low noise to preserve the sensitivity of the system. The LIT may function by detecting only relative shifts in the reflected beam as it scans across the surface and as the surface is translated under the beam, but it is advantageous to detect absolute reflectivity. The use of reflected light and a portion of the LAS light for inspection rather than total scattered light allows a simplified approach and avoids the problems involved in trying to capture all of the scattered light. The use of reflected light allows detection of absorption changes and defects associated therewith.

Figure 3:
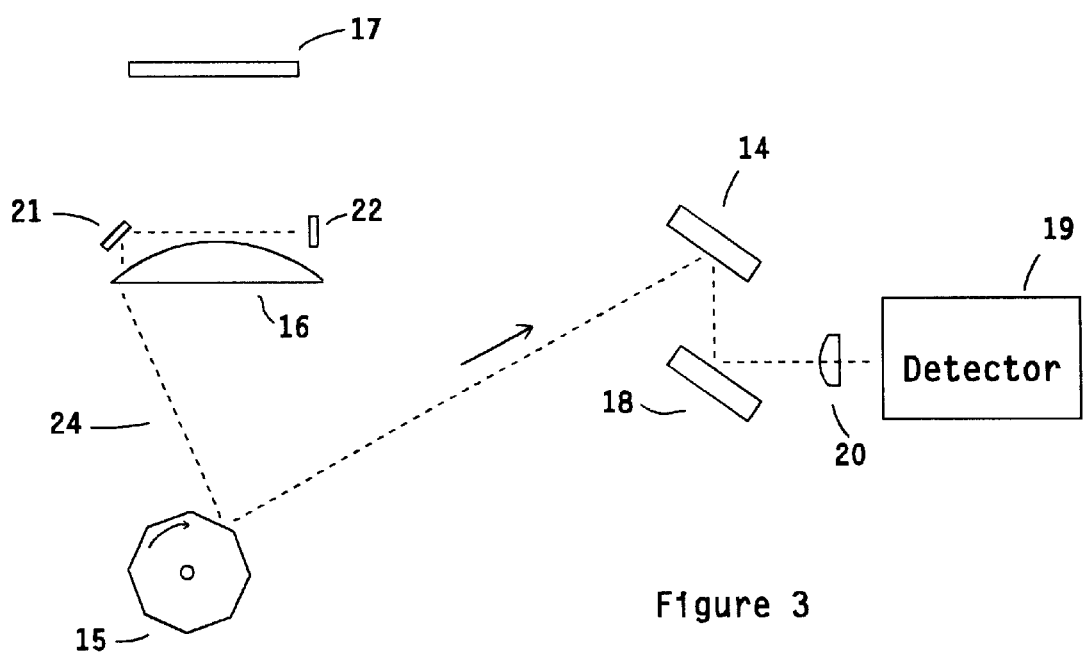
FIG. 3 shows the optical elements in the path for the reflected beam from the calibration mirrors.

FIG. 3 shows an optional feature which provides a start of scan signal and allows the detector to be calibrated to measure the absolute amplitude of the reflected beam. Measurement of the absolute reflectivity allows an additional class of defects and/or characteristics to be detected and/or measured, thus enhancing the capability of the tool. Calibration mirrors 21 and 22 are arranged so that an initial portion of the scan line falls on mirror 21 which reflects the beam to mirror 22 which reflects the beam back to mirror 21 and back into the TLA along the path for the reflected beam as described above. The length of the path of the beams going to and from the calibration mirrors is set equal to the length of the beam paths to and from the surface 17 to prevent spot size change. This arrangement creates a reference signal from the detector for each scan line which signals the start of the scan and is also known to correspond to maximum possible magnitude of the reflected beam. Alternatively a mirror could be positioned adjacent to the object being scanned to allow the beam to strike the mirror during the scan, but positioning the calibration mirrors away from the disk as shown in FIG. 3 is preferable since it reduces the number of fragile components near the mechanical moving parts. Having the maximum reference signal for comparison allows the amplitude of the reflected beam from the disk to be converted to an absolute measure of reflectivity. The signal from the calibration mirrors can be used as a start of scan without using it as an absolute amplitude reference. Once the beam strikes the Calibration Mirror 21 the reflected beam will slew to its maximum value. This transition from no reflected beam to the maximum forms a sharp edge in the analog output of the detector which can be used as the start of scan signal. A fixed delay can then be used to gauge the approximate time at which the scan line will be at the first data point on the disk. To avoid having false triggering from the other transitions in the signal at the edges of the disk, the circuitry which detects the start of scan signal should delay resetting until the scan line has cleared the last edge of the disk.

The Calibration Mirror 21 will produce essentially zero LAS light and, moreover, there are no mirrors to capture any LAS light. Therefore, during the calibration period, the signal from the LAS light detector will be at a minimum value. The reflected beam calibration can be used to judge laser power fluctuations which will also affect the intensity of the LAS light for a given feature. The reflected beam calibration can, therefore, be used to indirectly calibrate the LAS light signal.

Figure 4:
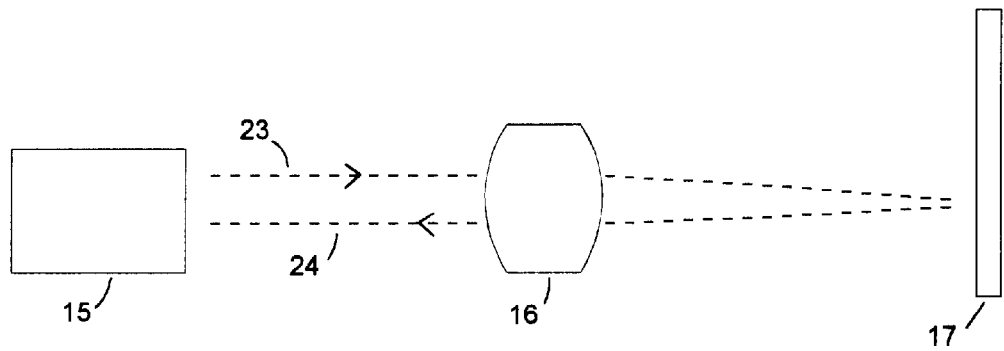
FIG. 4 shows the spatial relationship between the incident beam and the reflected beam between the surface and polygon mirror.
Figure 5:
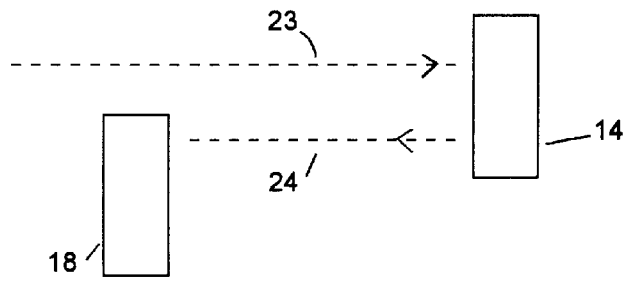
FIG. 5 shows the spatial relationship between the incident beam, the reflected beam and the capture mirror.

FIG. 4 shows the preferred spatial relationship between the incident beam and the reflected beam between the surface 17 and polygon mirror 15. As previously noted the reflected beam 24 is offset from the incident beam 23 to allow the reflected beam to be routed to the detector. This is achieved by causing the incident beam to strike the surface at a slight angle which causes the reflected beam to come off at a slight angle as shown in the FIG. 4. As an example, an offset angle of a few degrees over a 125 mm path results in a beam offset of on the order of 5-10 mm which easily allows the reflected beam to be routed to a mirror which is by-passed by the incident beam. The telecentric aspect of the TLA causes the reflected beam 24 to be essentially parallel to incident beam 23 after the reflected beam has passed through the TLA. The optical axis of the TLA should ideally split the angle formed by the incident and reflected beam at the surface to minimize the effects of coma and spherical aberration due to the beam separation. FIG. 5 shows the spatial relationship between the incident beam and the reflected beam in relation to the Capture Mirror 18 and Steering Mirror 14. The incident beam 23 passes above the Capture Mirror 18 on its way to Steering Mirror 14. The reflected beam 24 is sufficiently offset to allow it to strike Capture Mirror 18 and to be routed to the detector. This arrangement is deemed superior to using a beam splitter with the signal losses associated therewith. It is feasible to allow the incident and reflected beam to be coincident until the reflected beam can be separated using an appropriate beam splitter, but the arrangement shown is deemed preferable. Beam splitters which could be used if desired include polarizing beam splitters, partially reflective beam splitters, or pellicle beam splitters.

Figure 6:
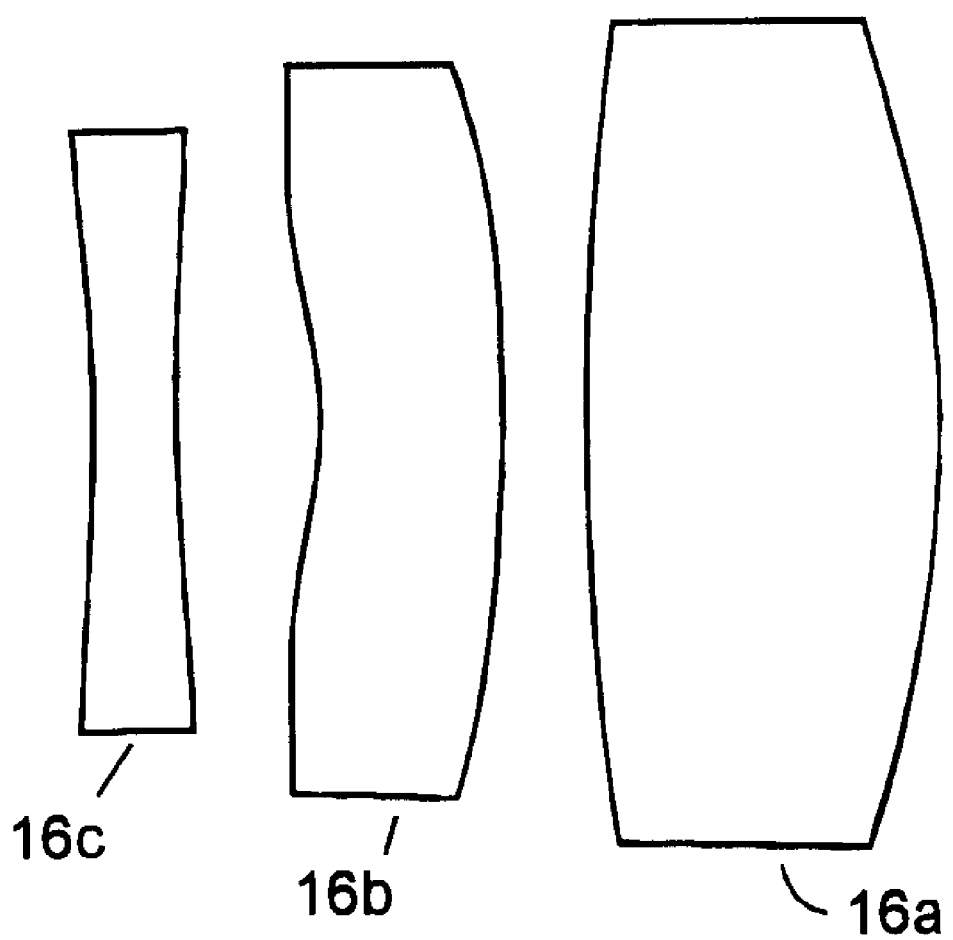
FIG. 6 shows a representative three lens implementation of the telecentric lens assembly.

The TLA's characteristics are tailored to the specifics of the application and particularly to the size of the surface being inspected. One standard size of disk for use in disk drives is 95 mm in diameter. For such a surface the design of the TLA could be specified for the wavelength of the laser being used as a field of 105 mm, focal length 125 mm, telecentricity <0.5 degrees and field curvature of <1.0 mm. FIG. 6 illustrates a three element spherical lens implementation which can be used to meet these requirements. Other implementations (including a single lens) may be used. An optical configuration which is capable of scanning 95 mm disks is also capable of being used to scan smaller disks. When smaller objects are being scanned it may be desirable to increase the sampling rate in order to obtain the same number of pixels for the smaller object.

Figure 7:
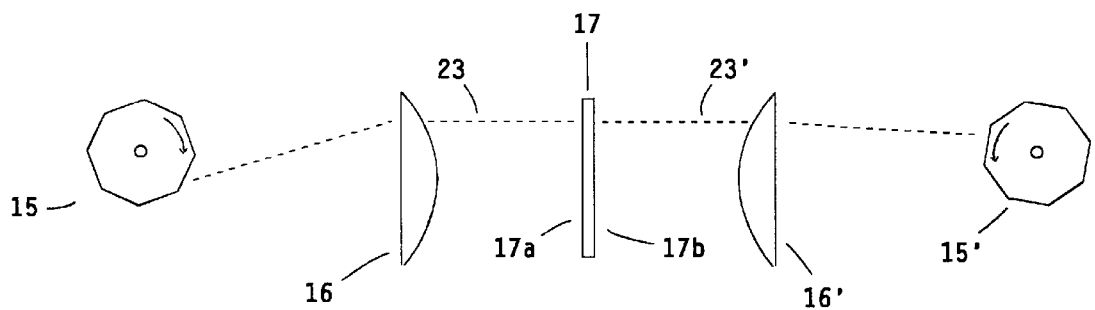
FIG. 7 shows the polygon scanner orientations in a two channel embodiment.

A preferred two channel arrangement is shown in FIG. 7. FIG. 7 shows the polygon scanner orientations in a two channel embodiment where the polygons 15, 15' are coplanar, but spin in opposite directions which results in the two incident beams 23, 23' maintaining a fixed relationship to each other as they scan planar surfaces 17a and 17b. It is also preferred that the rotational position of the two polygonal scanners be synchronized, but with one being advanced or retarded in time to avoid interference when the beams scan across the hole in the center of the disk.

Large Angle Scattered (LAS) Light Capturing

Figure 8:
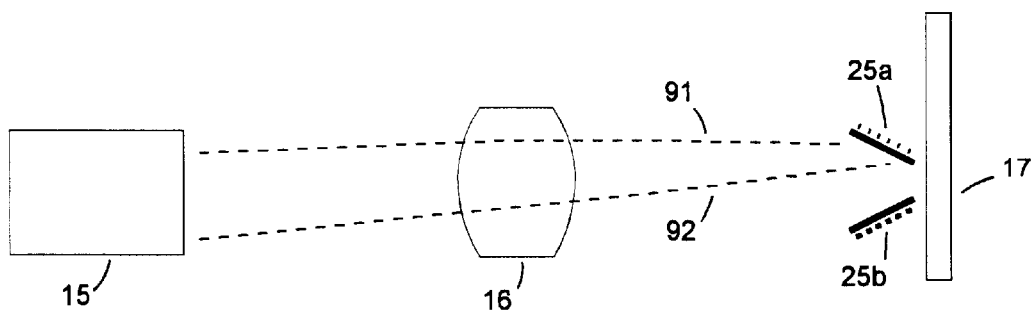
FIG. 8 is a side view of the plano mirrors for capturing the large angle scattered light in relation to the disk, TLA and scanner and the optical path of the light from one of the plano mirrors.
Figure 9:
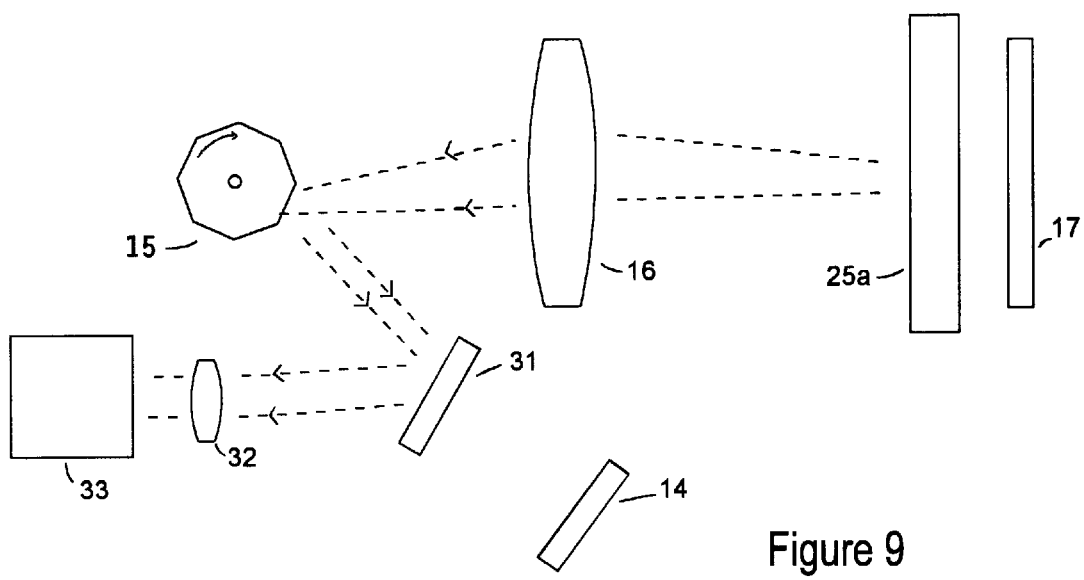
FIG. 9 is a top view of the plano mirrors for capturing the large angle scattered light and the optical path of the light from the plano mirrors to the detector.

FIG. 8 is a side view showing the plano mirrors 25a, 25b (LAS mirrors) used for capturing the LAS light. The LAS mirrors are placed above and below the scan line so that at least a portion of the LAS light from the disk 17 will be incident upon the mirrors and will then be reflected back through the TLA 16. The dashed lines 91, 92 illustrate the limiting ray paths for the LAS light reflected from the upper plano mirror 25a to the polygon scanner 15. The upper and lower bounds of the LAS light cone are determined in part by the upper and lower edges of the polygon facets. The ray paths from the lower plano mirror 25b are similar to those for mirror 25a. The LAS light from the two plano mirrors is superimposed on the polygon facet and effectively merged at that point. FIG. 9 is a top view of the LAS light optical path. This view shows that the plano mirrors are essentially rectangular and extend along the entire scan line. From the top, only mirror 25a can be seen. The limiting rays 93 and 94 are the outer edges of the LAS light cone as viewed from the top. After being reflected off of the polygon, the LAS light and the reflected beam are superimposed and must be separated by a beam splitter 31. The beam splitter 31 can conveniently be a mirror with an aperture which allows the incident and reflected beam to pass while redirecting the LAS light for separate detection. Lens 32 optionally can be included in the path of the LAS light to reduce the size of the LAS light cone before it strikes detector 33. The LAS light is detected the same way as the reflected light by preferably a silicon detector which produces an analog signal proportional to the intensity of the light striking it.

Data Capture and Analysis

Figure 12:
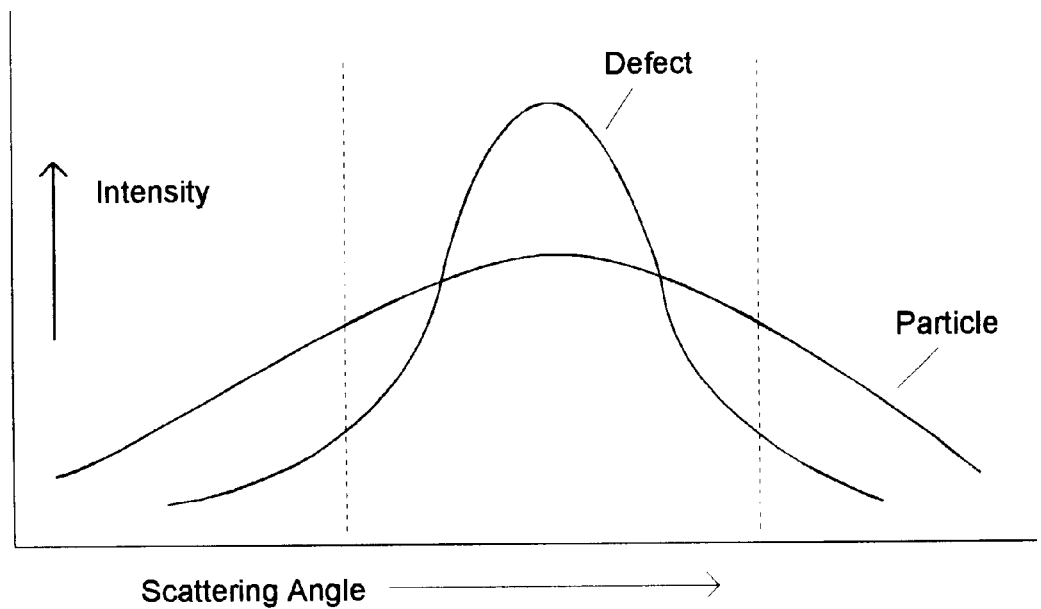
FIG. 12 is a graph of the intensity of light scattered by a particle and a surface defect versus scattering angle.

FIG. 12 illustrates the differing scattering characteristics of a surface adhering particle vesus a true defect. This difference can be used in the analysis of the image data to avoid false rejections. As shown in FIG. 12, the vertical axis is the intensity of the light being detected and the horizontal axis is the scattering angle. The plot for the particle shows a broad curve illustrating that the particle scatters light with fairly even intensity over a large range of scattering angles. The plot for the defect shows a relatively sharp peak illustrating that the peak intensity of the scattering is larger than for the particle and is distributed over a smaller scattering angle. The dotted vertical lines are intended to form a region in which the area under the two curves is equal which shows that a detection system which was only capable of measuring the light in this narrow range of scattering angles would be incapable of distinguishing the particle from the true defect. By analyzing the rate of change in the pixel data in the scattered light image, the system can look for the signature of a particle versus a defect, i.e., the system can determine whether the rate of change in the scattered light exceeds a selected threshold indicating a true defect.

Figure 10:
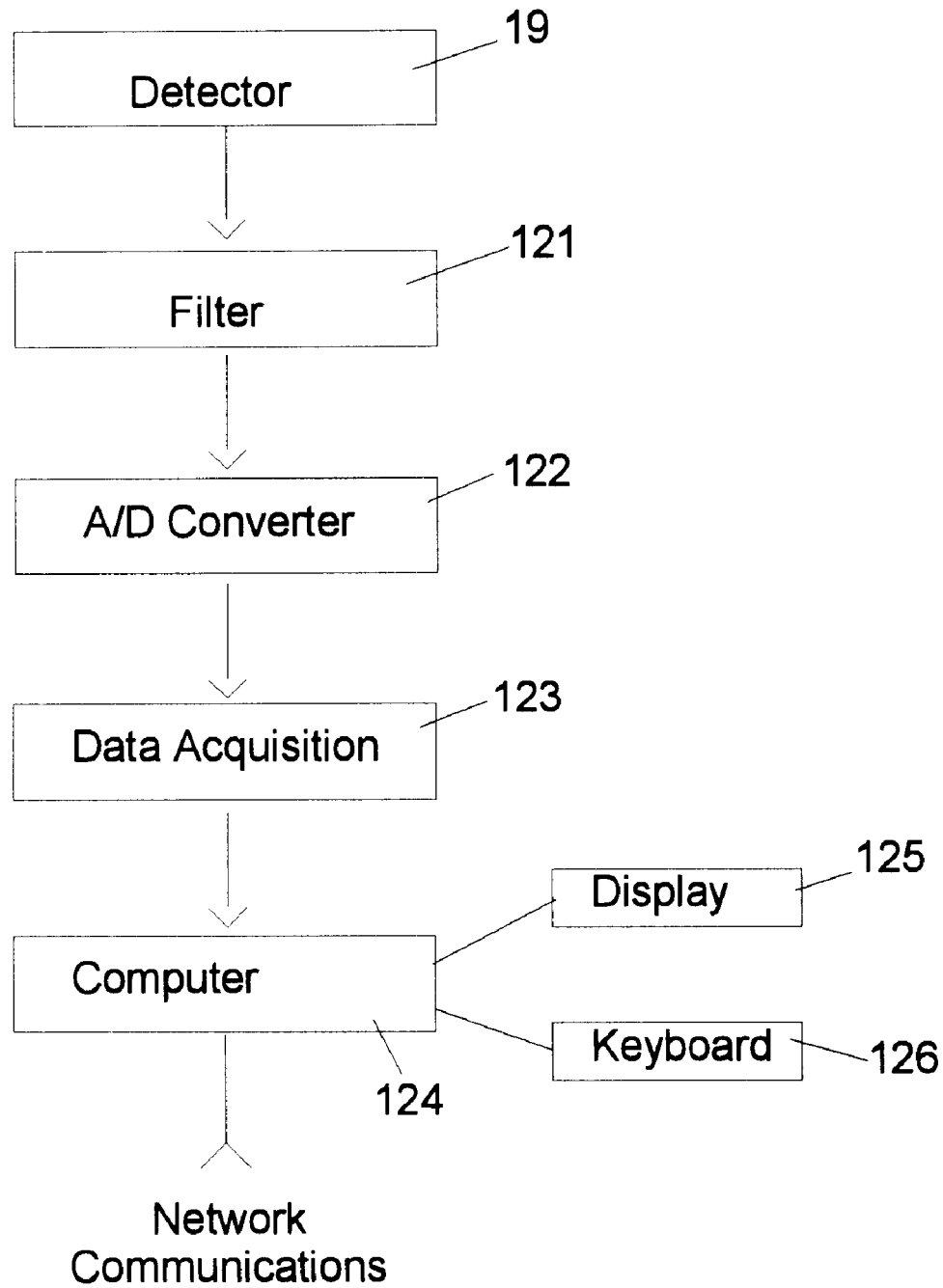
FIG. 10 illustrates the data path from a detector into the computer.

FIG. 10 illustrates a possible data acquisition path for one channel of an LIT. Since the two detectors 19, 33 are essentially the same, the hardware and firmware required for pixelating the signal from each detector is similar. FIG. 10 shows the path from detector 19, but the path from detector 33 is similar. The analog signal from the detector 19 is optionally filtered by filter 121 before being sampled and digitized by the A/D converter 122 to get a value for the reflectivity at the sample points. The sampling rate should be selected in coordination with the time required for each scan line and the desired resolution. For example, if the usable portion of each scan line requires 1 ms and a resolution of 2000 pixels per line is wanted, then a sampling rate of 2 MHz is needed. The spacing between the scan lines is the distance that the disk moves vertically during one scan. If 2000 vertical pixels are desired for a 95 mm disk, then the vertical movement should be about 47.5 microns per scan. Each digital sample value represents one pixel in the image of the surface of the disk. The data acquisition hardware 123 places the pixel data in a buffer which is accessible by the computer 124. Since the surface is scanned in lines, the pixel data is organized into lines as well. Since data acquisition is a common requirement, there are commercially available cards which can be plugged into slots in a PC, e.g., PCI bus slots, which will perform the required function at a sufficiently high rate. The A/D unit may also be included on such a card. The computer which processes that data can be any general purpose computer or workstation which has sufficient speed to process the data in the time allowed, e.g., within a few seconds. The data acquisition path for the data from the second channel, if present, should be identical to the one shown. The computer can process the data for the two detectors if it is fast enough. A single computer can also process two channels, i.e., four detectors, but it is also feasible to use separate computers for each channel. If separate computers are used, the results can be communicated from the B-channel computer to the A-channel computer which can then act upon the consolidated results by rejecting the disk or reporting the results through the network communication facilities to the master floor control system. At least one computer in the system should have a display 125 on which the enhanced image(s) can be displayed as well as messages, etc. Similarly at least one keyboard 126 should be available to allow parameter entry, manual control, maintenance, etc.

If the optional calibration mirrors are used, then the first portion of each scan line will correspond to maximum reflection and can be used as a reference signal for finding absolute reflectivity and as a start of scan signal for the hardware. The abrupt signal change which corresponds to the edges of the disk can be used to find the position of the edges in the line of data. For lines which cross the central hole in the disk there are four edges, otherwise there are two edges per line. Since it is not desirable to test 100 percent of the surfaces of the disks, provision has been made to exclude portions of each line by use of a mask. This could be done on a pixel by pixel basis with a flag bit for each pixel indicating whether it should be processed or not, but this method requires a relatively large amount of storage. A preferable approach is to record start and stop points in a table for each scan line. Using four numbers per line, e.g. x1, y1, x2, y2 allows the software to exclude the first x1 pixels in the line on the disk from processing, then process all pixels until pixel y1 is reached at which point processing is suspended again until pixel x2 and then continues until pixel y2 where processing of the line stops. The set of these numbers corresponding to the shape of the image of the disk being scanned will be called the mask. Since the mask is referenced to the edge of the disk, it must be located on pixel data in the buffer. The image of the disk in buffer does not always appear at the same place for various machines, times, etc. and, therefore, there is a need to fit the mask to the particular data by finding (or predicting) the location of the edges. Note that even though the disks are circular it is possible that the image of the disk may be elliptical due to artifacts of the system. For a line with only two edges and no laser bump texture only two numbers are required in the mask, since there is no need to skip over an area in the center of the disk, but it may be convenient to have four numbers for each line for simplicity. If an object other than a disk with a single central hole were to be scanned by the system, the mask could be adjusted accordingly by adding or removing numbers to cover the maximum number of the starts and stops required.

Figure 11:
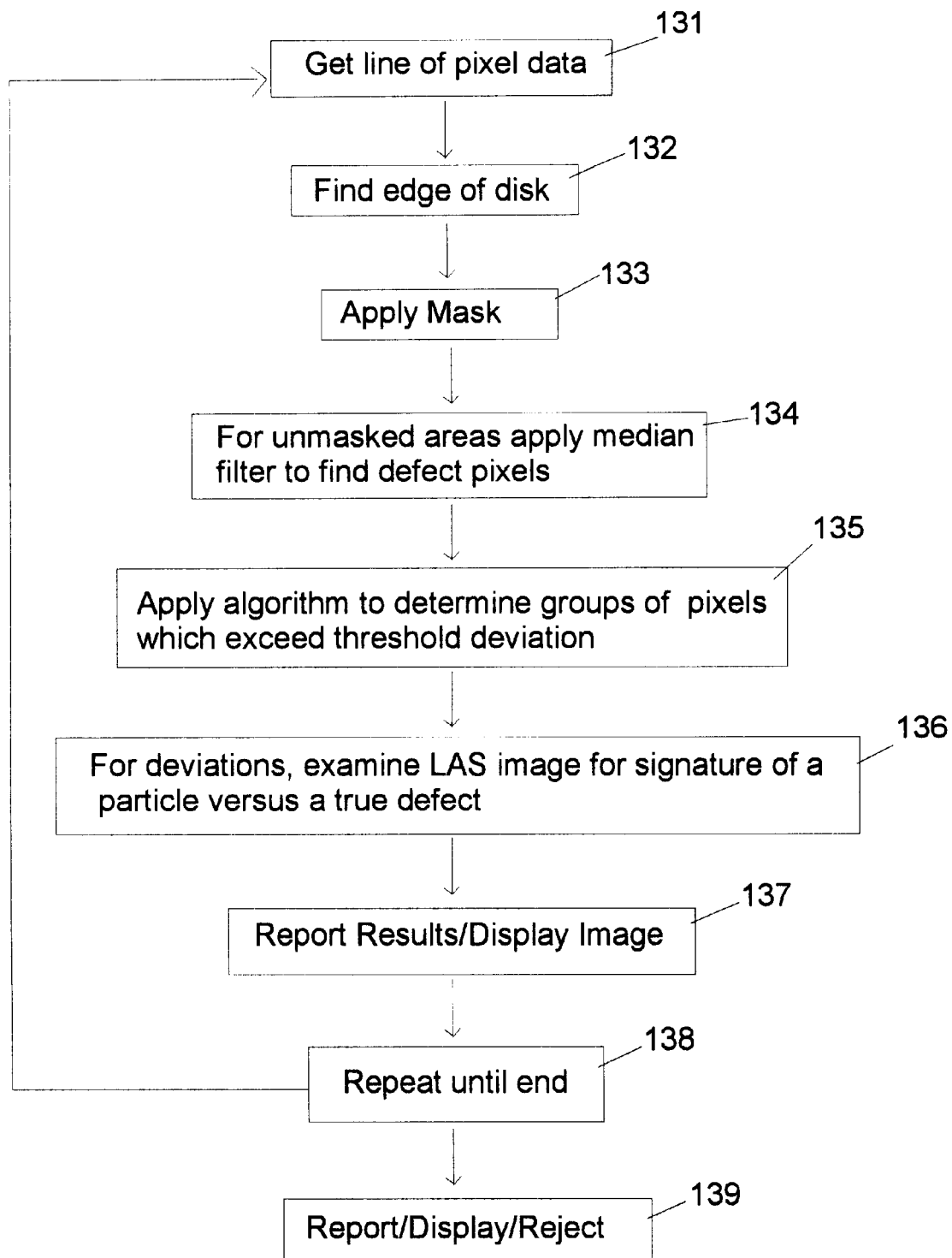
FIG. 11 is a flow chart of a method for processing the data.

FIG. 11 is a flow chart illustrating the data analysis. Initially the data is processed one line at a time, so the pixel data from detectors 19 and 33 is read line-by-line 131 to build the images in the computer's buffer. The process is repeated until the last lines of the images have been obtained 138. The edge of the disk in the reflected image line is found 132. The mask is applied to the line starting with the edge 133. The unmasked portions of each scan line in the reflected image are processed for defects by use of median filter 134. A selected number of pixels (e.g. 30–150) in a sliding window are averaged. A threshold above and below this running median is used to define a defect pixel. This threshold should be selected empirically at a level which most accurately finds true defects. A deviation of only a few percent (e.g. 3–4%) might be appropriate for a very uniform surface of a disk. However, single defect pixels are not generally significant for disks and may only be noise, so it is desirable to define an additional filter which looks for groups of defect pixels 135. Requiring that a predetermined number (e.g. 5–10) of consecutive defect pixels might be a simple way to achieve this, but could be sensitive to signal to noise problems. It is preferable that consecutive pixels not be required. A preferable analysis looks at the total number of defects in a selected region which can be a sliding window. The appropriate parameters for the window size and percentage of defect pixels which are tolerable should be determined empirically based on the particular application. The selected parameters should be programmable by operator input, but, for example, setting the threshold to 6 defect pixels out of a 3×3 pixel block might be typical for a magnetic disk scanning application. It has been found, however, that as the signal to noise ratio of the system increases, the need for a regional determination decreases. Another way to look at the data is to compute the maximum defect region size for the entire surface and compare this size to a selected threshold. Any standard statistical analysis of a pixel group of any size up to the entire surface which determines the probability that a particular deviation is due to chance can be used. A practical application of the LIT will probably use multiple tests of the sort described to define any number of defect signatures in the pixel data. Because the thresholds may need to be changed and experiments done to find the optimum value, they should be made programmable by operator input.

One optional method for looking for defects is to find the rate of change in the reflectivity using the derivative of the pixel stream. It has been discovered that a particular type of disk defect called a stain is not detectable using the median filter described above, but is detectable using the derivative because they are associated with a rapid change in reflectivity from one level to another. The second level of reflectivity persists for a relatively large distance so it is not seen as a defect using the median filter. Thresholds for the rate of change to be detected as a defect should likewise be defined empirically and be programmable.

Once the processing of the reflected image finds a suspected defect, the scattered light image is used as an additional test or filter to avoid false rejects due to particles adhering to the surface which will be removed later in the manufacturing process 136. Surface particles will produce deviations in the scattered light image which correspond to the deviation in the reflected image.

For highest processing speed or greatest throughput, the data acquisition process and data analysis can be performed simultaneously or concurrently. In order to accomplish this, the data analysis must a) check for valid data and b) predict mask location in the buffer, before all edges have been discovered. The presence of valid data in the buffer can be ascertained by querying the data acquisition electronics for amount of data transferred (if that capability exists as it does in some commercially available systems) or by timing. Prediction of mask location is performed with the knowledge that the disk shape does not change from disk to disk and that only small changes in disk position will occur. Given this, the edges discovered in the first 10% of the disk image are used to adjust the mask positions within certain limits. The analysis of the data in the buffer can then proceed even though the scan of the disk is not complete.

A disk that is flagged as defective can be handled in various ways including simply displaying the image 137 or automatically rejecting the disk 139. It is, of course, possible to build the capability into the LIT to sort the defective disks from the passing disks. It is also feasible to simply record the test results by carrier serial number and disk position and place the defective disks back into the carrier along with the passing disks. The results data can be electronically communicated to a shop floor control system or some form of printout or other marker might be attached to the carrier. The data could then be used to sort disks at a later time. One advantage of delaying the actual sorting of the disks to a subsequent time is that it allows the final decision to take additional tests into account and, thereby increases the flexibility of the system.

Another optional test that can be applied to the pixel from a finished disk which has sputtered thin films (or similar surfaces) is to select a set of areas distributed over the surface which are composed of multiple pixels and determine the average reflectivity of each area. If the average reflectivity of the selected areas varies more than a selected threshold, it may indicate a failure of the sputtering process to uniformly coat the disk. This type of test must be tuned empirically to the specifics of the surface being inspected and the process by which the surface is created.

The LIT system described herein is capable of detecting defects without human assistance, but an optional feature provides a display of the enhanced image(s) of the disk surface(s). There are a virtually unlimited number of ways that the pixel and defect data can be displayed in the form of an image. Obviously the magnitude of the pixel data can be converted to display intensities and/or colors for both the reflected image and the LAS light image. The defect pixels and areas should be displayed in a distinguishable manner, e.g. red dots on a gray background. It might be useful to have a display option which displays the difference between the reflected and LAS images. If the derivative option is being used, then the map of the derivative value could be displayed rather than or in addition to the absolute value of the pixels. The mask could also be displayed, as well as the identified textured area. Display of the data is considered to be a very powerful option which allows human pattern recognition to supplement and monitor the functioning of the tool when desired.

The various inventions described herein have been illustrated in their preferred embodiments, but variations within the scope of the inventions will be apparent to those of skill in the art.

We claim:

1. An apparatus for detecting defects in planar surfaces of a object comprising:

a laser for generating a beam (A-beam) along a first path;

a telecentric lens assembly including one or more lenses;

a first rotating mirror for scanning the A-beam through the first telecentric lens assembly and across at least a portion of a first planar surface along a first scan line, the A-beam being directed to strike the first planar surface of the object with a portion of the A-beam forming a reflected beam (A/R-beam) passing back through the telecentric lens assembly and being reflected off of the first rotating mirror along a second path;

a first plano mirror arranged along the first scan line and at an angle from the planar surface of the object to reflect a portion of any light scattered as the A-beam scans across the scan line back onto the first rotating mirror and along the second path forming a first cone of scattered light;

a beam splitter in the second path which separates the first cone of scattered light from the A/R-beam;

a first light detector arranged to produce a first analog signal proportional to the intensity of the A/R-beam; and a second light detector arranged to produce a second analog signal proportional to the intensity of the first cone of scattered light.

2. The apparatus of claim 1 further comprising a second plano mirror arranged symmetrically to the first plano mirror along the first scan line to reflect a second cone of scattered light as the A-beam scans across the first scan line back onto the rotating mirror and along the second path.

3. The apparatus of claim 1 further including a B-channel for inspecting a second planar surface of the object comprising:
   a second telecentric lens assembly including one or more lenses;
   a second rotating mirror for scanning a B-beam through the second telecentric lens assembly and across at least a portion of the second planar surface along a second scan line, the B-beam being directed to strike the second planar surface of the object with a portion of the A-beam forming a second reflected beam (B/R-beam) passing back through the second telecentric lens assembly and being reflected off of the second rotating mirror along a third path;
   a second plano mirror arranged along the second scan line and at an angle from the second planar surface of the object to reflect a portion of scattered light as the B-beam scans across the second scan line back onto the second rotating mirror and along the third path forming a second cone of scattered light;
   a second beam splitter in the third path which separates the second cone of scattered light from the B/R-beam;
   a third light detector arranged to produce an analog signal proportional to the intensity of the B/R-beam; and
   a fourth light detector arranged to produce an analog signal proportional to the intensity of the second cone of scattered light from the B/R-beam.

4. The apparatus of claim 3 further comprising a third plano mirror arranged symmetrically to the first plano mirror along the first scan line to reflect a third cone of scattered light as the A-beam scans across the first scan line back onto the first rotating mirror and along the second path; and a fourth plano mirror arranged symmetrically to the second plano mirror along the second scan line to reflect a fourth cone of scattered light as the B-beam scans across the second scan line back onto the second rotating mirror and along the third path.

5. The apparatus of claim 3 further comprising a lifter for the object which moves the object through the A-beam and B-beam simultaneously while leaving substantially all of the first and second planar surfaces unobscured from the A-beam and B-beam.

6. The apparatus of claim 1 further comprising a first and second analog to digital converters for digitizing the first and second analog signals to generate pixel data forming a reflected light image and a scattered light image of the first planar surface.

7. The apparatus of claim 6 further comprising means for analyzing the reflected light image for deviations from uniformity and examining corresponding portions of the scattered light image to distinguish particles from surface defects.

8. The apparatus of claim 1 further comprising at least one mirror arranged to reflect an initial or terminal portion of the A-beam to generate a reference signal for determining the absolute reflectivity of the first planar surface.

9. The apparatus of claim 1 wherein the A-beam strikes the first planar surface at an angle which results in the A/R-beam being offset from the A-beam.

10. The apparatus of claim 1 further comprising a reducing lens which reduces the size of the cone of scattered light striking the second detector.

11. A method for inspecting a planar surface of an object comprising the steps of:
    directing a first laser beam (A-beam) onto a rotating mirror;
    repeatedly scanning the A-beam reflected from the rotating mirror through a telecentric lens assembly and across a first scan line in an inspection area;
    moving the object through first the scan line in the inspection area;
    sampling the intensity of a first reflected beam (the A/R-beam) from the first scan line from a first planar surface of the object as reflected back through the telecentric lens assembly to form pixel data representing a reflected light image of the first planar surface; and
    sampling the intensity of large angle scattered (LAS) light from a plano mirror positioned along the scan line which reflects a portion of the the LAS back through the telecentric lens assembly to form pixel data representing a scattered light image of the first planar surface.

12. The method of claim 11 further comprising the steps of:
    analyzing the pixel data representing the reflected light image for groups of pixels which deviate by more than a selected threshold amount from surrounding pixels to determine suspected defects; and
    analyzing pixel data representing the scattered light image corresponding to the suspected defects to determine whether suspected defect is actually a particle on the surface.

13. An apparatus for forming a reflected light image and a scattered light image of a planar surface of a object comprising:
    a laser for generating a beam along a first path;
    a telecentric lens assembly including one or more lenses in the first path;
    a lifter which moves the object through an inspection area in the first path;
    a rotating mirror in the first path for scanning the beam through the first telecentric lens assembly and across at least a portion of a planar surface of the object along a scan line, the beam being directed to strike the planar surface of the object substantially perpendicular so that a portion of the beam is reflected forming a reflected beam passing back through the telecentric lens assembly and being reflected off of the rotating mirror along a second path;
    first and second plano mirrors positioned along the scan line, offset from the beam and the reflected beam, the first and second plano mirrors being symmetrically disposed on opposites sides of the scan line and at an angle from the planar surface of the object to reflect first and second portions of scattered light through telecentric lens assembly and onto the rotating mirror and along the second path forming a cone of scattered light;
    a beam splitter in the second path which separates the cone of scattered light from the reflected beam;

a first light detector arranged to produce a first analog signal proportional to the intensity of the reflected beam;

a second light detector arranged to produce a second analog signal proportional to the intensity of the cone of scattered light; and a second data acquisition system which samples and digitizes the second analog signal to produce pixel data in a buffer corresponding to a scattered light image of the planar surface.

14. The apparatus of claim 13 further comprising a display on which at least one of the reflected light image or the scattered light image is viewable.

15. The apparatus of claim 13 further comprising means for applying a median filter to the pixel data in the reflected image to determine groups of defect pixels which differ from surrounding pixels by more than a threshold amount.

16. The apparatus of claim 15 further comprising means for analyzing a portion of the scattered light image corresponding to a group of defect pixels to determine a rate of change in the scattered light image; and means for determining that the defect pixels correspond to a particle if the rate of change is below a selected threshold.

* * * * *